United States Patent
Gottenbos et al.

(10) Patent No.: US 9,248,079 B2
(45) Date of Patent: Feb. 2, 2016

(54) METHOD FOR CLEANING DENTAL PLAQUE FROM TEETH USING AN ADHERENT PEELABLE GEL

(75) Inventors: Bart Gottenbos, Budel (NL); Jozef Johannes Maria Janssen, Herten (NL)

(73) Assignee: Koninklijke Philips N.V., Eindhoven (NL)

(*) Notice: Subject to any disclaimer, the term of this patent is extended or adjusted under 35 U.S.C. 154(b) by 685 days.

(21) Appl. No.: 12/672,710

(22) PCT Filed: May 8, 2008

(86) PCT No.: PCT/IB2008/051835
§ 371 (c)(1),
(2), (4) Date: Feb. 9, 2010

(87) PCT Pub. No.: WO2008/135957
PCT Pub. Date: Nov. 13, 2008

(65) Prior Publication Data
US 2010/0221196 A1    Sep. 2, 2010

Related U.S. Application Data

(60) Provisional application No. 60/916,353, filed on May 7, 2007.

(51) Int. Cl.
*A61K 8/00* (2006.01)
*A61Q 11/00* (2006.01)
*A61K 8/04* (2006.01)
*A61K 8/73* (2006.01)

(52) U.S. Cl.
CPC .............. *A61K 8/042* (2013.01); *A61K 8/736* (2013.01); *A61Q 11/00* (2013.01); *A61K 2800/5426* (2013.01)

(58) Field of Classification Search
None
See application file for complete search history.

(56) References Cited

U.S. PATENT DOCUMENTS

| | | | |
|---|---|---|---|
| 4,659,700 A * | 4/1987 | Jackson | 514/55 |
| 4,902,227 A * | 2/1990 | Smith | 433/215 |
| 5,000,942 A | 3/1991 | Libin | |
| 5,310,563 A | 5/1994 | Curtis et al. | |
| 5,711,938 A * | 1/1998 | Larm | 424/49 |
| 5,989,569 A * | 11/1999 | Dirksing et al. | 424/401 |
| 2003/0003421 A1 * | 1/2003 | Bestenheider et al. | 433/215 |
| 2003/0219390 A1 | 11/2003 | Santarpia, III et al. | |
| 2004/0238391 A1 * | 12/2004 | Pond | 206/369 |
| 2005/0058744 A1 * | 3/2005 | Steinberg et al. | 426/3 |
| 2005/0175959 A1 | 8/2005 | Jodaikin et al. | |

FOREIGN PATENT DOCUMENTS

| | | |
|---|---|---|
| EP | 0563013 A2 | 9/1993 |
| EP | 1190720 A1 | 3/2002 |
| WO | WO 9015592 A1 * | 12/1990 |
| WO | 0100044 A1 | 1/2001 |
| WO | 0211681 A1 | 2/2002 |
| WO | 03042251 A1 | 5/2003 |
| WO | 2003059302 A1 | 7/2003 |

OTHER PUBLICATIONS

A. Chenite, C. Chaput, D. Wang, C. Combes, M.D. Buschmann, C.D. Hoemann, J.C. Leroux, B.L. Atkinson, F. Binette, A. Selmani. Novel injectable neutral solutions of chitosan form biodegradable gels in situ. Biomaterials 21 (2000) 2155-2161.*
Hiroshi Sano, Ken-Ichiro Shibasaki, T Akashi Matsitkubo, and Yoshinori Takaesu. Effect of Molecular Mass and Degree of Deacetylation of Chitosan on Adsorption of *Streptococcus Sobrinus* 6715 to Saliva Treated Hydroxyapatite. Bull Tokyo Dent. Coli., vol. 43, No. 2, pp. 75-82, May 2002.*
R. J. Gibbons, E. C. Moreno, and I. Etherden. Concentration-Dependent Multiple Binding Sites on Saliva-Treated Hydroxyapatite for *Streptococcus sanguis*. Infection and Immunity, Jan. 1983, p. 280-289.*

* cited by examiner

*Primary Examiner* — Frederick Krass
*Assistant Examiner* — Michael P Cohen

(57) ABSTRACT

The method for cleaning dental plaque biofilm from the teeth includes the steps of applying a liquid gellable composition to the teeth, the composition including a positively charged polymer such as chitosan, the liquid composition having a viscosity which results in coverage of substantially all of the exposed areas of the teeth. The liquid composition is then gelled by the addition of a second composition, such as a negatively charged compound. The resulting gelled composition has an adherence to the plaque biofilm which is greater than the adherence between the biofilm and the teeth. The gel layer with the biofilm is peeled off of the teeth, removing the dental plaque.

7 Claims, No Drawings

METHOD FOR CLEANING DENTAL PLAQUE FROM TEETH USING AN ADHERENT PEELABLE GEL

TECHNICAL FIELD

This invention relates generally to cleaning dental plaque from teeth, and more specifically concerns use of a gel substance to remove the dental plaque.

BACKGROUND OF THE INVENTION

Various devices and methods are known for removing dental plaque from teeth, which is a critical aspect of maintaining oral health and for preventing tooth decay. These include both manual and power toothbrushes, and various other systems using air and/or water. These devices operate with varying degrees of success, often depending upon the skill and persistence of the user. These known prior art devices often fall short of complete cleaning of all the teeth, frequently leaving dental plaque on some areas of the teeth which are hard to reach by typical use. The failure to remove all the existing dental plaque creates a risk for the user relative to tooth decay and a decrease in oral health. Hence, it is desirable that a device, system or method of dental plaque removal be developed which is capable of reliably, and without undue skill on the part of the user, removing dental plaque from all exposed areas of the teeth.

SUMMARY OF THE INVENTION

Accordingly, a method for cleaning dental plaque biofilm from teeth comprises the steps of: applying a liquid gelable composition to the teeth, the composition having a viscosity such that substantially all exposed areas of the teeth are coverable by the liquid composition; gelling the liquid composition on the teeth to produce a gel layer, wherein the gel layer adheres more strongly to the dental plaque biofilm than the biofilm adheres to the teeth; and removing the gel layer from the teeth, and the dental plaque biofilm along with the gel layer, wherein the dental plaque biofilm adheres to the gel layer.

BEST MODE FOR CARRYING OUT THE INVENTION

In a first step of the present method, a liquid composition having particular characteristics is applied to the teeth. The liquid must have a viscosity which permits the material to readily cover all of the exposed areas of the teeth. The liquid further must have the characteristic that its components adhere strongly to the dental plaque biofilm. In general, positively charged polymer compositions are preferred. The bacteria present in the biofilm typically has a negative surface charge, as well as the material on the surface of the bacteria in the biofilm. Positively charged polymers will adhere strongly to the dental plaque biofilm through electrostatic interactions. A specific example of a suitable positively-charged polymer is a chitosan solution. Some other examples include diethyleneiminoethyl dextran, polyethyleneimine, chitin, polylysine and poly(dimethyldiallylammonium chloride).

The liquid composition can be applied to the teeth with various devices, including a mouthpiece which is configured to surround the teeth combined with a pump or syringe for injecting the liquid composition into the mouthpiece. The liquid composition is thereby applied to all exposed surfaces of the teeth, including exposed areas between the teeth (interproximal areas).

Other devices for applying the liquid composition include various brushing devices, including conventional power or manual toothbrushes. Still further, a sprayer could be used. Other known devices can also be used, as long as they are capable of applying the liquid composition to all exposed areas of the teeth.

As indicated above, chitosan is a suitable liquid. In one specific example, 3 grams of chitosan is stirred into 100 ml of demineralized water and 2 ml of lactic acid, to enable dissolving of the chitosan and for ease of application. Chitosan is a preferred composition because it is non-toxic. However, it should be understood that other compositions can be used, including basically any positively charged polymer, as discussed above. It is important, however, that the positively charged compounds in the liquid composition adhere strongly to the dental plaque biofilm on the teeth.

In the next step of the method, the liquid is converted into a gel substance. This can be done in various ways. In one application, a selected second solution is applied to the liquid composition which is in place on the teeth as a result of the first step to produce a gelling of the liquid composition. Examples of known compositions or compounds which are capable of such a result are multiple negative charged or alkalic compounds. NaOH, sodium carbonate, sodium triphosphate and glycerol phosphate are examples of compounds which result in the liquid on the teeth being set into a solid or strong gel. The resulting gel must adhere to the dental plaque biofilm with a higher adhesive force than the adhesive force between the biofilm and the teeth. Accordingly, when the gel is removed, the plaque biofilm comes away from the teeth, with the gel and the biofilm remaining in adherent contact with each other.

In addition to a second compound being used to produce the gelling of the liquid on the teeth, other ways of gelling the liquid can be used. One example is to increase the pH of the liquid on the teeth. Another example is to increase the temperature of the liquid on the teeth to the point where it gels. Other means can be used as well depending upon the nature of the liquid composition on the teeth. The resulting gel must exhibit the characteristic of stronger adherence between the gel and the biofilm than between the biofilm and the teeth.

As a further optional step at this point, a backing member, like a thin bandage, can be added to the outer surface of the gel layer, making removal of the gel and biofilm easier.

The next step in the process is to peel the gel layer off of the teeth, taking the dental plaque biofilm layer with it. This can either be done by hand, or with the assistance of an instrument, such as various conventional dental probes or a toothbrush. Since the gel layer is present on all exposed areas of the teeth, when all the gel is removed, dental plaque from all those same exposed areas is also removed. The teeth are thus effectively cleaned of all dental biofilm for all areas initially exposed to the liquid composition. The peeled gel and biofilm may then be disposed of.

Accordingly, a method has been disclosed in which a liquid gelable composition is first applied to the teeth and then gelled, such as by the application of a second compound or other means. The gelled material is then removed, taking with it the dental plaque biofilm on the teeth. The liquid composition covers all exposed areas of the teeth; the gelled layer adheres to the biofilm more strongly than the biofilm adheres to the teeth.

Although a preferred embodiment of the invention has been disclosed here for the purposes of illustration, it should be understood that various changes, modifications and substitutions may be incorporated in the embodiment without departing from the spirit of the invention, which is defined by the claims which follow.

What is claimed is:

1. A method for cleaning dental plaque biofilm from teeth, comprising the steps of:
   applying a first liquid composition to the teeth, the first liquid composition comprising a positively charged polymer of diethyleneaminoethyl dextran having a viscosity such that substantially all exposed areas of the teeth are coverable by the first liquid composition;
   thereafter, applying a second liquid composition to the first liquid composition, the second liquid comprising a negatively charged compound, wherein the second liquid composition causes the first liquid composition to gel on the teeth to produce a peelable gelled layer, in adherent contact with the biofilm, wherein the gelled layer adheres more strongly to the dental plaque biofilm than the biofilm adheres to the teeth; and
   removing the gelled layer from the teeth by peeling the gelled layer off of the teeth, wherein the dental plaque biofilm remains in adherent contact with the gelled layer as the gelled layer is removed, cleaning the dental biofilm from all areas exposed to the liquid composition.

2. The method of claim 1, wherein the first liquid composition is applied with a brush member.

3. The method of claim 1, wherein the first liquid composition is applied with a mouthpiece which substantially surrounds the teeth of the user in combination with a pump or syringe for injecting the first liquid composition into the mouthpiece.

4. The method of claim 1, wherein the positively charged polymer in the first liquid composition adheres to the plaque biofilm by electrostatic interaction.

5. The method of claim 1, including an additional step of applying a backing member to an outer surface of the gelled layer prior to removing the gelled layer with the biofilm from the teeth.

6. The method of claim 1, wherein the negatively-charged compound is a multiple negative charged or an alkaline compound.

7. The method of claim 1, wherein the negatively-charged compound is selected from sodium hydroxide, sodium carbonate, sodium triphosphate and glycerol phosphate.

* * * * *